United States Patent [19]

Onoda

[11] Patent Number: 4,951,133

[45] Date of Patent: Aug. 21, 1990

[54] ENDOSCOPE LIGHT SOURCE APPARATUS

[75] Inventor: Fumiyuki Onoda, Fuchuu, Japan

[73] Assignee: Olympus Optical Co., Ltd., Tokyo, Japan

[21] Appl. No.: 376,458

[22] Filed: Jul. 7, 1989

[30] Foreign Application Priority Data

Oct. 15, 1988 [JP] Japan .................. 63-260019

[51] Int. Cl.$^5$ .................. H04N 7/18; H04N 5/33; A61B 1/06
[52] U.S. Cl. .................. 358/98; 358/113; 128/6
[58] Field of Search .............. 358/98, 901, 113, 110; 128/4, 6; 361/293, 18

[56] References Cited

U.S. PATENT DOCUMENTS

| 4,621,284 | 11/1986 | Nishioka et al. | 358/98 |
| 4,740,837 | 4/1988 | Yanagisawa et al. | 358/98 |
| 4,807,026 | 2/1989 | Nishioka et al. | 358/98 |
| 4,816,909 | 3/1989 | Kimura et al. | 358/98 |
| 4,866,526 | 9/1989 | Ams et al. | 358/98 |
| 4,878,113 | 10/1989 | Nakamura | 358/98 |
| 4,885,635 | 12/1989 | Kimura et al. | 358/98 |

*Primary Examiner*—John K. Peng
*Attorney, Agent, or Firm*—Armstrong, Nikaido, Marmelstein, Kubovcik & Murray

[57] ABSTRACT

An endoscope light source apparatus to which a fiberscope or an electronic endoscope can be connected is removably provided with a rotary filter apparatus on an optical axis connecting a light source emanating illuminating light and an illuminating light emanating end for feeding a connected scope with the illuminating light output from the light source. In case the rotary filter apparatus is inserted, the rotary filter apparatus has a rotary filter which sequentially transmits the illuminating light of a specific wavelength from the light source. Furthermore, the apparatus has a plurality of character filters on the optical axis and is provided with a character changing apparatus which changes the character of the illuminating light from the light source by selectively interposing the character filter on the optical axis corresponding to the connected scope.

12 Claims, 12 Drawing Sheets

ENDOSCOPE LIGHT SOURCE APPARATUS

BACKGROUND OF THE INVENTION

1. Field of the Invention

The present invention relates to an endoscope light source apparatus which can feed illuminating light to a scope provided with a frame sequential type imaging means, a scope provided with a synchronous type imaging means and a fiberscope (optical scope).

2. Related Art Statement

Recently, there is extensively used an endoscope (called also a scope in the following) whereby, by inserting an elongate insertable part through a body cavity, organs within the body cavity can be observed and as required, by using a treating tool inserted through a treating tool channel, various curing treatments can be made. As an endoscope, there are suggested optical type endoscopes (called also fiberscopes in the following) wherein an image is transmitted by a bundle of optical fibers and observed with the naked eye and electronic type endoscopes (called also electronic scopes in the following) wherein an image is taken by such a solid state imaging device of such a charge coupled device (CCD). Furthermore, an endoscope can be classified into a frame sequential type electronic scope which sequentially switches incident light for an imaging device to color light of such as R(red), G(green) and B(blue) in each picture, and a synchronous type electronic scope which makes each picture element of the imaging device a disposition of such as R, G and B by providing mosaic filters of such as R, G and B on the front surface of the imaging device.

That is to say, in the frame sequential type electronic endoscope, illuminating light from a light source is fed to a light guide sequentially through color transmitting filters which transmit the colors such as R, G and B so that an object is illuminated by the illuminating light of R, G and B sequentially transmitted by the light guide and imaged. On the other hand, in the synchronous type electronic scope, an object is illuminated by white light transmitted through the light guide and imaged by the solid state imaging device provided with mosaic filters. In this manner, the illuminating method of the frame sequential type electronic scope is different from the illuminating method of the synchronous type electronic scope and the light source which feeds illuminating light adapted itself to each scope is needed.

Then, in the official gazette of Japanese Patent Laid Open No. 2927/1987, it is proposed that one apparatus feeds illuminating light adapted to each scope by means of making a rotary filter having R, G and B color transmitting filters possible to be retreated from an optical axis. That is, in case the frame sequential type electronic scope is used, the rotary filter is interposed on the optical axis, and in case the synchronous type electronic scope and fiberscope are used, the rotary filter is retreated from the optical axis.

However, the illuminating light from the light source is reduced through transmitting the color transmitting filter of the rotary filter. The quantity of illuminating light fed to the light guide when the frame sequential type electronic scope is used, is different from the quantity of the illuminating light when the synchronous type electronic scope is used. Therefore, when the frame sequential type electronic scope is used, the quantity of light might be insufficient, and also, there was a problem that an incident end of the light guide is burnt when the synchronous type electronic scope and fiberscope are used.

Further, since it is impossible to obstruct the infrared rays of illuminating light sufficiently in the color transmitting filters, there was a problem that the color reproducibility in the frame sequential type electronic scope is not sufficient because of a spectral sensitivity characteristics of the solid state imaging device.

OBJECT AND SUMMARY OF THE INVENTION

An object of the present invention is to provide an endoscope light source apparatus which can feed illuminating light to a scope provided with a frame sequential type imaging means, a scope provided with a synchronous type imaging means and a fiberscope whereby the naked eye observation is possible.

The endoscope light source apparatus of the present invention is provided with a light source emanating illuminating light, an illuminating light emanating end for feeding a connected scope with the illuminating light output from the light source, a rotary filter apparatus removably provided on an optical axis connecting the light source and the illuminating light emanating end having a rotary filter sequentially transmitting light of a specific wavelength of the illuminating light from the light source in case the rotary filter apparatus is inserted on the optical axis and a character changing apparatus having a plurality of character filters and changing a character of the illuminating light from the light source by selectively interposing the character filters on the optical axis corresponding to the connected scope.

BRIEF DESCRIPTION OF THE DRAWINGS

FIGS. 1 to 11 relate to the first embodiment of the present invention and FIG. 1 is a perspective view showing the formation of an endoscope light source apparatus related to the embodiment.

FIGS. 13 to 16 relate to the third embodiment of the present invention and FIG. 13 is a perspective view showing the formation of an endoscope light source apparatus of the embodiment.

DETAILED DESCRIPTION OF THE PREFERRED EMBODIMENTS

Embodiments of the present invention will be explained on referring to the drawings as follows.

FIGS. 1 to 11 show the first embodiment of the present invention.

Figure 1:
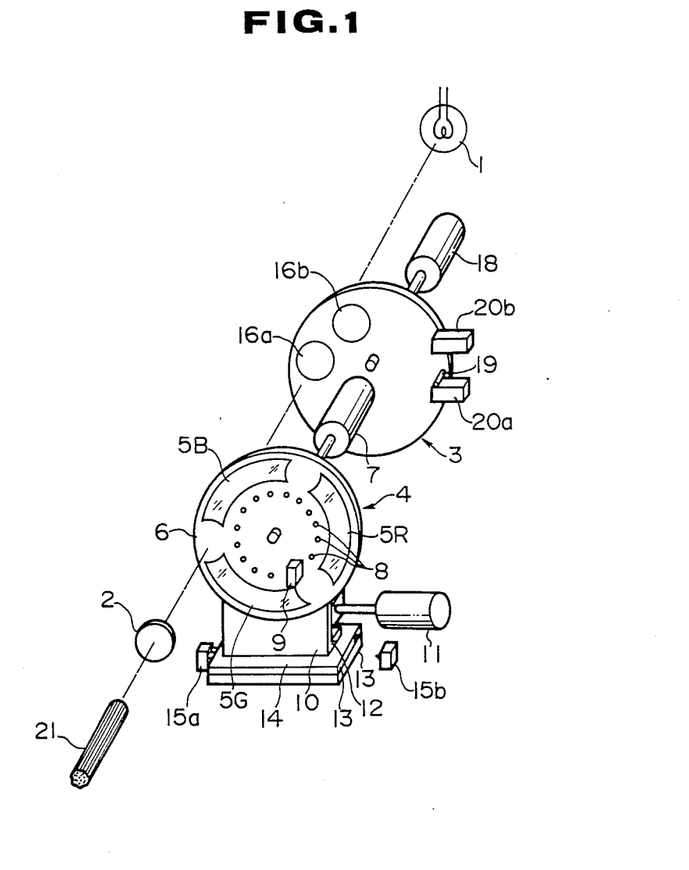

As shown in FIG. 1, a turret 3, a rotary filter 4 and a condenser lens 2 which converges light are interposed between a light source lamp 1 emanating white light and a light guide 21. A rotary filter 4 has color transmitting fan-shaped filters 5R, 5G and 5B for transmitting three primary colors of R, G and B, respectively, in the peripheral direction of a filter frame 6 so that the filter 4 is driven by a motor 7. Further, on the filter frame 6, many holes 8 are provided as encoder indices in the peripheral direction. On both sides of the plate of the filter frame 6, for example, a light emitting device and a position detecting sensor 9 such as a photosensor are arranged. A position detecting rotary encoder is formed of these holes 8 and the position detecting sensor 9, and the motor 7 is controlled based on the signal from the position detecting sensor 9.

The rotary filter 4 is fitted to a plate-like fitting bracket 10 and the fitting bracket can be moved by a motor 11. That is to say, below this fitting bracket 10, a horizontally bent flange part 12 is formed, and below this flange part 12, fixed two parallel rails 13 are provided. At the bottom of the flange part 12, a plate-like sliding part 14 in the form of holding these rails from the right and left is formed. The sliding part 14 is fitted slidably to the rail 13 so that the rotation for rotating the above mentioned motor 11 normally and reversely is transmitted by such a gear which is not illustrated and the sliding part 14 is guided and moved by the rail 13 so as to move the rotary filter 4. On both sides of the moving direction of the rotary filter 4, flat prismatic switches 15a and 15b are fixed. These switches 15a and 15b have pressing parts, respectively. In case the sliding part 14 moves and presses these pressing parts, a control signal is output so as to stop the rotation of the motor 11. Further, in case the rotary filter 4 is located in the position of the switch 15a as shown in FIG. 1, the color transmitting filters 5R, 5G and 5B are located on the optical axis between the light source lamp 1 and the light guide 21. If the rotary filter 4 is located on the side of the switch 15b, the rotary filter 4 is located in the place which is retreated from the optical axis.

In this embodiment, the turret 3 is interposed on the optical axis, too. In the peripheral direction of the turret 3, a first character filter 16a and a second character filter 16b are provided. The first character filter 16a reflects the character of the solid state imaging device along with the color transmitting filters 5R, 5G and 5B so as to be able to sufficiently obstruct infrared rays. Also, the second character filter 16b is a reducing light filter so as to reduce the predetermined amount of white light from the light source lamp 1.

The turret 3 rotates in normal and reverse directions by rotating a motor 18 normally and reversely so that the first character filter 16a or the second character filter 16b is interposed on the optical axis. On the rim of the turret 3, a pin 19 for position detecting is arranged. On the side of the turret 3, switches 20a and 20b are provided. If the pressing parts of the switches 20a and 20b which are not illustrated are pressed by the pin 19, the switches 20a and 20b output control signals so as to stop the rotation of a motor 18. Further, in case the pin 19 is arranged on the side of the switch 20a, the first character filter 16a is interposed on the optical axis as illustrated. In case the pin 19 is arranged on the side of the switch 20b, the second character filter 16b is interposed on the optical axis.

The optical axis between the light source lamp 1 and the light guide 21 is formed to make a right angle with the character filters 16a and 17b, and the color transmitting filters 5R, 5G and 5B. The rotary filter 4's rotation and movement for retreat and the turret 3's rotation are controlled by a rotary movement control apparatus 17 (see FIG. 4) mentioned in the following. In case the rotary filter 4 is not retreated, the white light enters the condenser lens 2 through the first character filter 16a and the color transmitting filters 5R, 5G and 5B, and further reaches the end surface of the light guide 21 formed of fiber bundles. Also, in case the rotary filter 4 is retreated in the direction separated from the optical axis, the white light from the light source lamp 1 is converged by the condenser lens 2 through the second character filter 16b.

These apparatuses of the embodiment are included in a control apparatus 42 of an endoscope apparatus shown in FIGS. 3a–3e. Besides these apparatuses, the control apparatus 42 contains a video processor processing video signals to which each type of scope (endoscopes) 31A, 31B, 31C, 31D and 31E can be connected. The scope 31A is a frame sequential type electronic scope. The scope 31B is a synchronous type electronic scope using color mosaic filters. The scope 31C is a fiberscope externally fitted with a frame sequential type television camera (which is mentioned as a fiberscope fitted with a frame sequential type television camera in the following). The scope 31D is a fiberscope externally fitted with a synchronous type television camera (which is mentioned as a fiberscope fitted with a synchronous type television camera in the following). The scope 31E is a fiberscope.

Respective scopes 31A, 31B, 31C, 31D and 31E have an elongate inserting part 33 and an operating part 34 connected to the rear end side of the inserting part 33. Further, the scopes 31A to 31E are provided with universal cords 35A to 35E extended from the operating part 34, respectively, and the tips of these universal cords 35A to 35E are provided with light source connectors 36A to 36E. Further, in the frame sequential type electronic scope 31A and the synchronous type electronic scope 31B, signal connectors 37A and 37B are provided on the tip side of the universal cords 35A and 35B, respectively. Also, in the fiberscope 31C fitted with a frame sequential type television camera and the fiberscope 31D, a frame sequential type television camera 39C and a synchronous type television camera 39D are fitted respectively to an eyepiece part 38 of the fiberscope 31E and the signal cables extended respectively from the television cameras 39C and 39D are provided at the tip respectively with signal connectors 40C and 40D.

A set of connector receptacles 41a and 41b are provided, for example, on the front surface of a housing of the control apparatus 42 so as to be able to set the respective scopes in a usable state by connecting the connectors 36A, 37A; 36B, 37B; 36C, 40C; 36D, 40D; and 36E respectively of these scopes 31A to 31E. The connector receptacle 41a is a light source connector receptacle and the connector receptacle 41b is a signal connector receptacle. That is, the light source connectors 36A to 36E are connected to the light source connector receptacle 41a and signal connectors 37A, 37B, 40C and 40D are connected to the signal connector receptacle 41b.

In case the fiberscope 31E is connected to the control apparatus 42 and used, an object is observed with the naked eye in the eyepiece part 38; however, in case the other scopes 31A to 31D are used, an image to be formed can be color-displayed by a color monitor connected to the signal output end of the control apparatus 42.

The inside formation of these scopes 31A to 31E is shown in FIGS. 4 to 8, respectively.

In these scopes 31A to 31E, the light guide 21 transmitting illuminating light is inserted and the illuminating light from the light source lamp 1 in the control apparatus 42 is fed to the incident end surface of the light guide 21 through the condenser lens 2. The incident illuminating light is transmitted to the emanating end surface side by the light guide 21, and further transmitted through a light distributing lens 44 arranged in front of this exit end surface (the tip part of the inserting part 33) so that the object side in front is illuminated.

In these scopes 31A to 31E, an objective 45 for forming an image is arranged in the tip part of the insertable part 33. In the image forming position of the objective 45, a solid state imaging device 46 such as a CCD is arranged in the frame sequential type electronic scope 31A and the synchronous type electronic scope 31B. The solid state imaging device 46 is a photoelectric conversion element and photoelectrically converts the optical image formed on the imaging surface into an electric signal which is fed to an output terminal 51 through a pre-amplifier 50. Further, on the front surface of the solid state imaging device 46 of the synchronous electronic scope 31B, a mosaic filter 49 is formed.

In the meantime, the fiberscope 31E and scopes 31C and 31D fitted with television cameras are provided with an image guide 47 and the incident end surface of the image guide 47 is arranged so as to face the image forming position of the objective 45. An eyepiece 48 is arranged as opposed to the emanating end surface of the image guide 47. In the fiberscope 31E, an object can be observed with the naked eye by bringing eyes close the eyepiece part 38. Also, in the scopes 31C and 31D fitted with a frame sequential type television camera 39C or a synchronous type television camera 39D on the eyepiece part 38, the solid state imaging device 46 is arranged as opposed to the eyepiece 48 through an image forming lens which is not illustrated. In the solid state imaging device 46, the optical image formed on the image forming surface is converted to electric signals by the photoelectric conversion and output. Also, in front of the solid state imaging device 46 of the scope 31D, the mosaic filter 49 is formed. The signal from the solid state imaging device 46 of the scopes 31A to 31D is conducted to each output terminal 51 through the pre-amplifier 50, respectively. Each output terminal 51 is connected to the signal connectors 37A, 37B, 40C and 40D (see FIG. 3) through a signal transmitting line and further connected to switching switches 52 in the control apparatus 42 through the signal connector receptacle 41b. Also, in the solid state imaging device 46, a solid state imaging device driving clock signal is applied from drivers 57 and 59, mentioned later, through a terminal 53.

The other scopes 31A to 31D than the fiberscope 31E are provided with type signal generating circuits 54A to 54D, respectively, which output scope discriminating type signals so that these scopes are connected to a discriminating circuit 55 in the control apparatus 42 through signal connectors 37A, 37B, 40C and 40D, respectively.

Furthermore, in the scopes 31A to 31E, a guide for transmitting gas and water, which is not illustrated, is provided with the light guide 21, and gas and water is transmitted in the guide for transmitting gas and water through the connector receptacle 41a and the light source connectors 36A to 36E.

Figure 4:
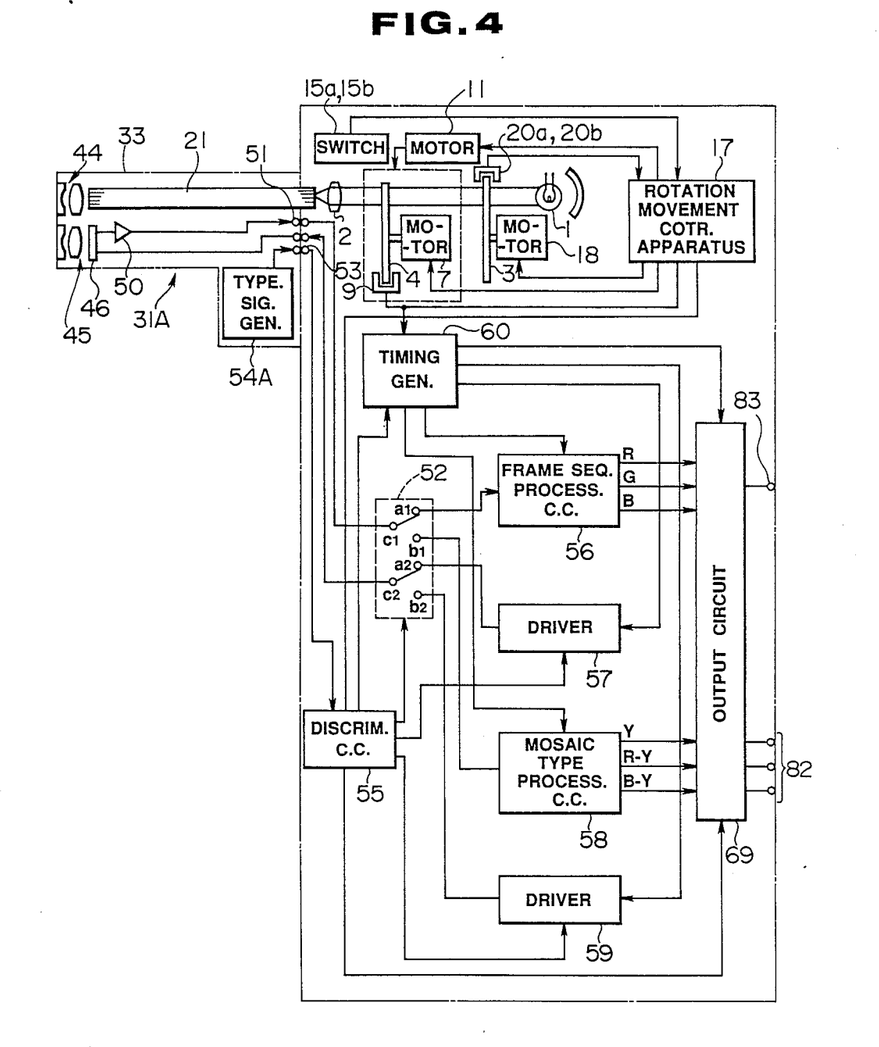
FIG. 4 is a block diagram showing the formation of a control apparatus of FIGS. 3a–3e.
Figure 5:
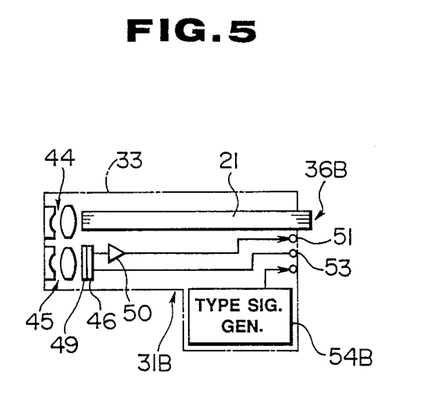
FIG. 5 is an explanatory view showing the formation of a synchronous type electronic endoscope.
Figure 6:
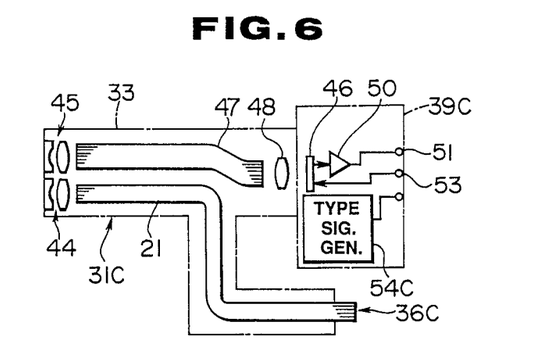
FIG. 6 is an explanatory view showing the formation of a fiberscope fitted with a frame sequential type externally fitted camera.
Figure 7:
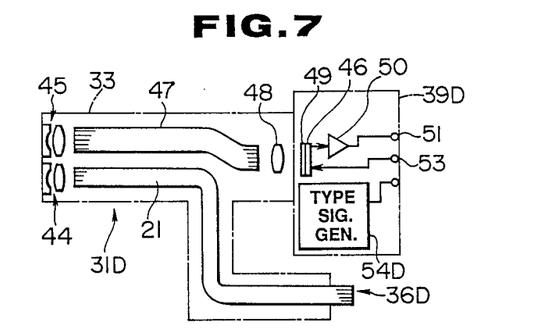
FIG. 7 is an explanatory view showing the formation of a fiberscope fitted with a synchronous type externally fitted camera.
Figure 8:
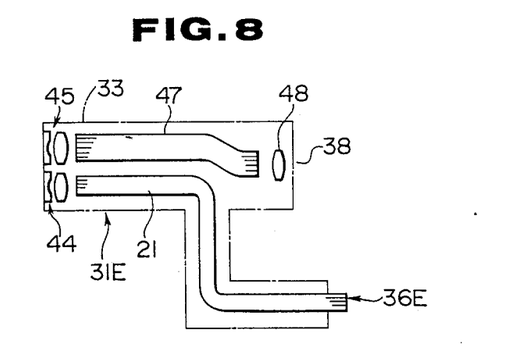
FIG. 8 is an explanatory view showing the formation of a fiberscope.

The formation of the control apparatus 42 is shown in FIG. 4.

The discriminating circuit 55 determines which scopes 31A to 31E are connected with a scope discriminating type signal from the type signal generating circuits 54A to 54D of the scopes 31A to 31D and outputs a discriminating signal. The rotary moving control apparatus 17 controls the motors 7, 11 and 18 based on the discriminating signal. That is to say, in case the discriminating signal showing that the scopes 31A and 31C are connected is fed into the rotary moving control apparatus 17, the motor 11 is rotated so as to interpose the rotary filter 4 on the optical axis and rotates the motor 7, and then, the motor 18 is rotated so as to interpose the first character filter 16a of the turret 3 on the optical axis. Also, in case the discriminating signal, showing that the scopes 31B, 31D and 31E are connected, is fed into the rotary moving control apparatus 17, the motor 11 is rotated so that the rotary filter 4 is retreated from the optical axis, and the second character filter 16b is interposed on the optical axis by rotating the motor 18. As mentioned above, these operations are also controlled by the signal from the switches 15a, 15b, 20a, and 20b, and the position detecting sensor 9.

Terminals 51 and 53 of the scopes 31A to 31D are connected to common ends c1 and c2 of the switches 52, respectively. Terminals a1 and b1 of the switches 52 are connected to a frame sequential type processing circuit 56 and a driver 57 and terminals a2 and b2 are connected to a synchronous type processing circuit 58 and a driver 59, respectively. The discriminating circuit 55 switches the switches 52 based on the type signal from type signal generating circuits 54A to 54D of the scopes 31A to 31D. By this operation, the signal from the output terminal 51 of the scopes 31A and 31C are input into the frame sequential type processing circuit 56 and the signal from the output terminal 51 of the scopes 31B and 31D are input into the synchronous type processing circuit 58.

Figure 9:
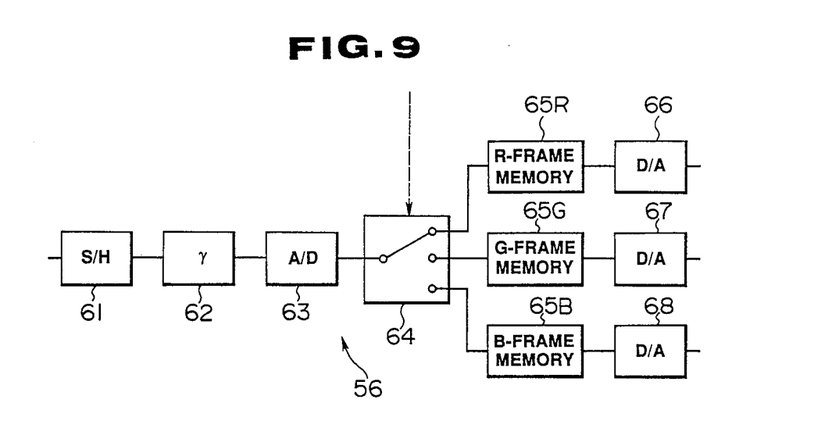
FIG. 9 is a block diagram showing the formation of a frame sequential type processing circuit.

The frame sequential type processing circuit 56 is formed, for example, as shown in FIG. 9.

The frame sequential type processing circuit 56 is controlled base on a timing generator 60 so that sequentially imaged signals under the illuminating light of each wavelength of R, G and B are converted into color signals R, G and B and goes into an output circuit 69. That is, the signal from the scopes 31A and 31C is fed into a sample holding circuit 61 and sample held. Furthermore, in a γ correcting circuit 62, the signal is γ corrected. In an A/D conversion circuit 62, the signal is converted into a digital signal and fed into a multiplexer 64. The multiplexer 64 is controlled by the signal from the timing generator 60, and a time sharing signal which is fed through scopes 31A and 31C, the sample holding circuit 61 and the A/D conversion circuit 63, are multiplexed. By this operation, the signals obtained under the illuminating light of R, G and B are written into an R frame memory 65R, a G frame memory 65G and a B frame memory 65B, respectively. The signal data written into these respective frame memories 65R, 65G and 65B, is simultaneously read out and converted into analog color signals in D/A converters 66 to 68, respectively, and then output to an output circuit 69.

Figure 10:
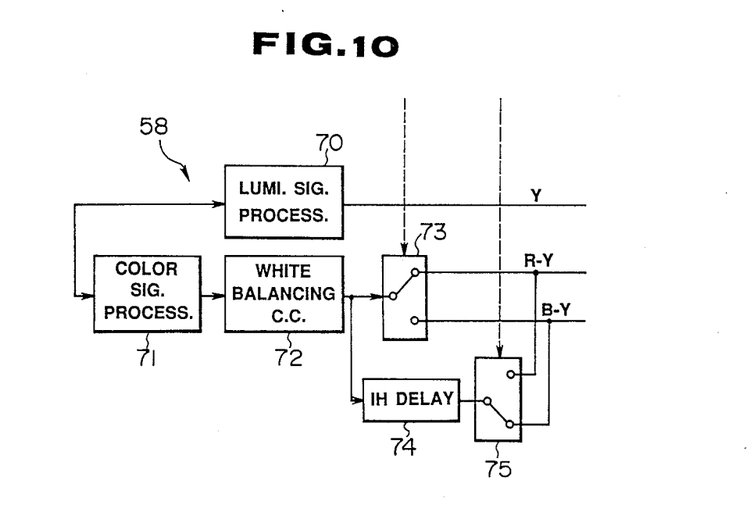
FIG. 10 is a block diagram showing the formation of a synchronous type processing circuit.

In the meantime, the synchronous type processing circuit 58 is formed, for example, as shown in FIG. 10.

The signals from the scopes 31B and 31D are fed into a luminance signal processing circuit 70 and a color signal regenerating circuit 71. In the luminance signal processing circuit 71, a luminance signal Y is produced and fed into the output circuit 69. From the color signal regenerating circuit 71, color-difference signals R−Y and B−Y are time-shared on each horizontal line and outputted so that the color-difference signals are white balance compensated in a white balance circuit 72 and fed into an analog switch 73 and a 1H delay line (H is a horizontal period) 74. The analog switch 73 is controlled by the signal from the timing generator 60 and the output of the analog switch 73 is switched on each 1H. The 1H delay line 74 is delayed by 1 horizontal period and is provided to an analog switch 75. The analog switch 75 is controlled by the signal from the timing generator 60 and the output of the analog switch 75 is switched on each 1H. Thus, continuous color-difference signals R−Y and B−Y are input into the output circuit 69 from the analog switches 73 and 75.

Figure 11:
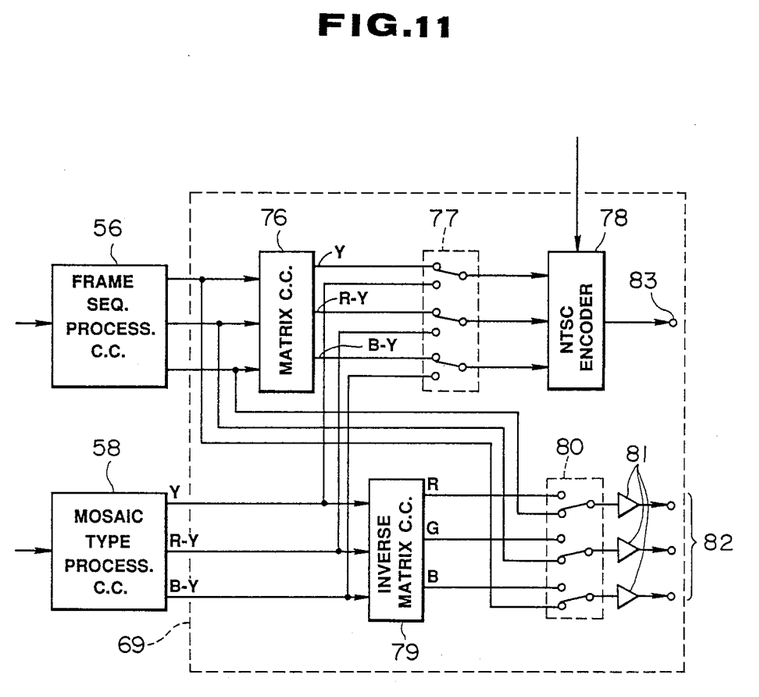
FIG. 11 is a block diagram showing the formation of an output circuit.

The output circuit 69 is formed, for example, as shown in FIG. 11.

The color signals R, G and B from the frame sequential type processing circuit 56 are fed into a matrix circuit 76 and switching switches 80. On the other hand, the luminance signal Y from the synchronous type processing circuit 58, and the color-difference signals R−Y and B−Y are fed into an inverse matrix circuit 79 and switching switches 77. The matrix circuit 76 obtains a luminance signal Y and color-difference signals R−Y and B−Y by making color signals R, G and B a matrix, and the inverse matrix circuit 79 obtains the luminance signal Y and color signals R, G and B from the color-difference signals R−Y and B−Y. The output of the switching switches 77 is fed into an NTSC encoder 78. The NTSC encoder produces a composite video signal of the NTSC system from the luminance signal Y and the color-difference signals R−Y and B−Y, and the composite video signal goes into an NTSC output terminal 83. The color signals R, G and B from the switching switches 80 goes into R, G and B output terminals 82 through buffers 81, respectively. Furthermore, these switching switches 77 and 80 can be manually switched and can be also switched by interlocking both switching switches 77 and 80.

The timing generator 60 outputs a timing signal based on the discriminating signal from the discriminating circuit 55 and the rotation of the rotary filter 4.

The terminals a1 and a2 or the terminals b1 and b2 are simultaneously selected by the switches 52, respectively. Therefore, in case a signal of scopes 31A and 31D is fed into the frame sequential type processing circuit 56 from the output terminal 51, the driver 57 supplies a driving pulse for the solid state imaging device 46 through the switches 52, and in case a signal is fed into the synchronous type processing circuit 58 from the output terminal 51, a driving pulse is supplied by the driver 59 through the switches 52. Further, the drivers 57 and 59 output a driving pulse based on the timing of the signal from the timing generator 60.

Figure 2A:
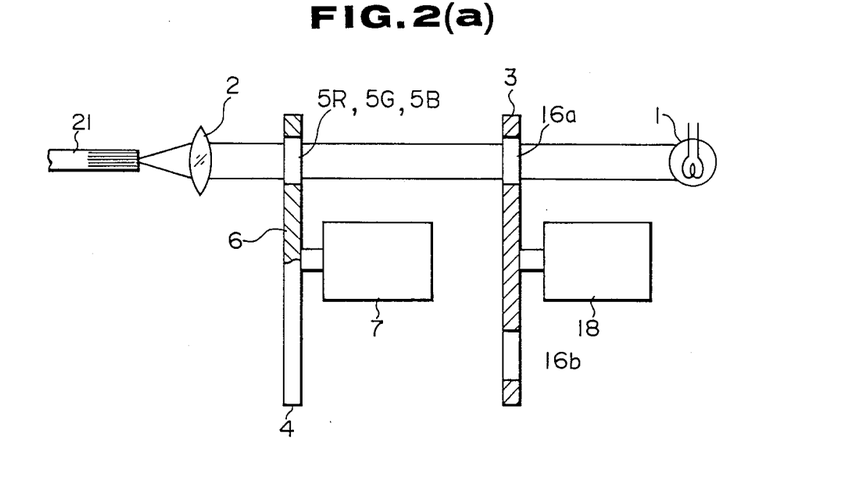
FIGS. 2a and 2b are explanatory view showing the operation of the embodiment.
Figure 2B:
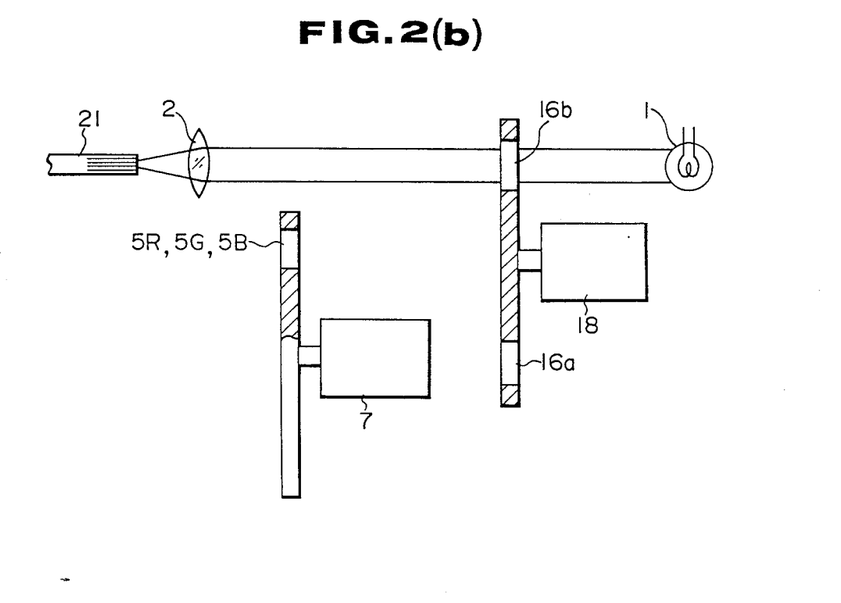
Figures 3A, 3B, 3C, 3D, 3E:
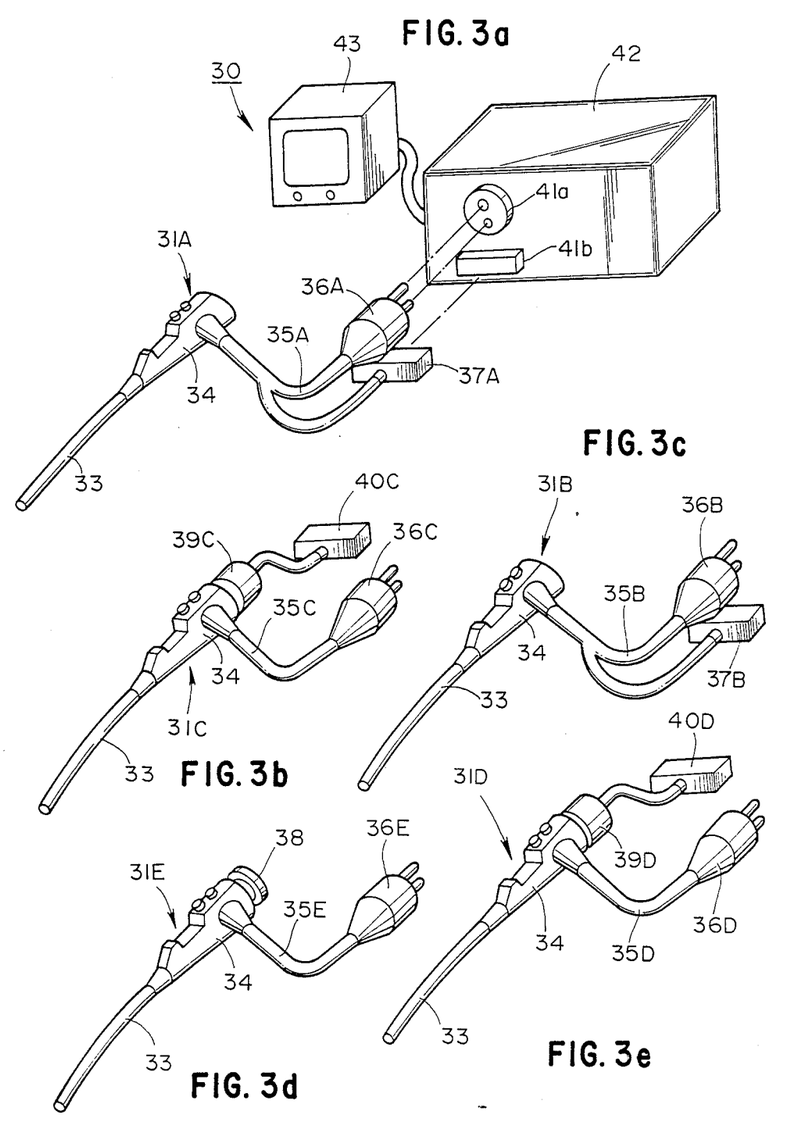
FIGS. 3a–3e are perspective views showing the entire system of an endoscope apparatus including an endoscope light source apparatus.

Next, the operation of the apparatus of this embodiment formed as described above, will be explained on referring to FIG. 2. FIG. 2(a) shows the state of the rotary filter 4 and the turret 3 in case the scopes 31A and 31C are connected. FIG. 2(b) shows the state of the rotary filter 4 and the turret 3 in case the scopes 31B, 31D and 31E are connected.

First, the frame sequential type electronic scope 31A and the fiberscope 31C fitted with the frame sequential type television camera are fitted with the control apparatus 42. Then, the discriminating signal showing the scopes 31A and 31C is output from the discriminating circuit 55 and color transmitting filters 5R, 5G and 5B of the rotary filter 4 are sequentially interposed on the optical axis by the rotary moving control apparatus 17 as shown in FIG. 2(a). Also, in this case, the first character filter 16a of the turret 3 is interposed on the optical axis so that the white light from the light source lamp 1 becomes suitable illuminating light for the solid state imaging device which is operated by the frame sequential type obstructing such as infrared rays. The white light is fed into the light guide 21 through the condenser lens 2.

On the other hand, in case the synchronous type electronic scope 31B, the fiberscope fitted with the synchronous type television camera and the fiberscope 31E are fitted with the control apparatus 42, the rotary filter 4 is retreated from the optical axis by the rotary moving control apparatus 17 as shown in FIG. 2(b). Then, the second character filter 16b is interposed on the optical axis by rotating the motor 18 by the rotary moving control apparatus 17. With this, the white light from the light source lamp 1 passes through the second character filter 16b and then the quantity of the light is reduced. Then, the white light is converged by the condenser lens 2. Thus, a burntout of the incident end surface of the light guide 21 can be prevented so that the white light becomes a suitable illuminating light, from which infrared rays are removed, for the scopes 31B, 31D and 31E.

The signals from the scopes 31A to 31D are fed into the frame sequential type processing circuit 56 or the synchronous type processing circuit 58 through the switch 52 and then, fed into the output circuit 69. Thus, the composite video signal of the NTSC system are fed from the output circuit 69 into the NTSC output terminal 83 and color signals R, G and B are output from the RGB output terminals 82. These signals are fed into a monitor apparatus 43 and displayed in color.

In this manner, in the first embodiment, the most suitable illuminating light (from which infrared rays were removed or the quantity of the light was reduced) for the scope to be used can be supplied by controlling the rotation and movement of the rotary filter 4 and the turret 3.

Figure 12:
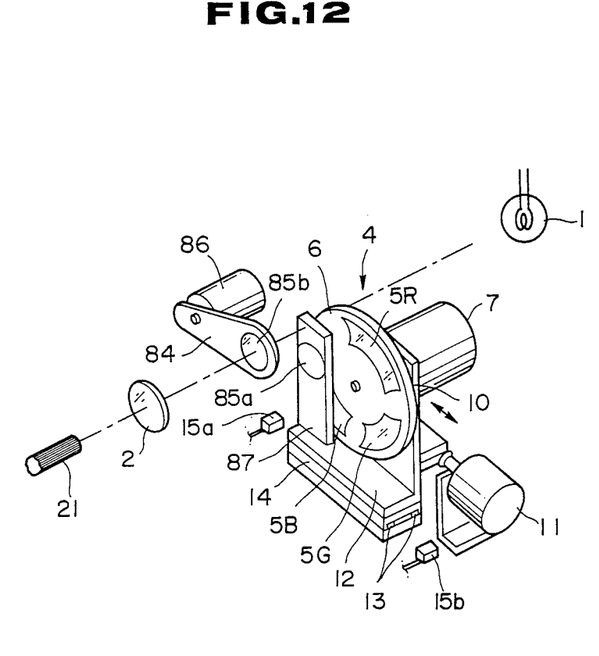
FIG. 12 is a perspective view showing an endoscope light source apparatus related to the second embodiment of the present invention.

FIG. 12 shows the second embodiment of the present invention. In FIG. 12, since the same elements of the formation as FIG. 1 are given the same reference numerals, the explanation of these elements will be omitted.

In this embodiment, a rotary arm 84 is provided in place of the turret 3. A second character filter 85b is provided in the rotary arm 84 which is provided on the rotary axis of a rotary solenoid 86 so that the rotary arm 84 can be rocked. The rotary solenoid 86 is controlled by the rotary moving control apparatus 17 in FIG. 4 so that the rotary arm 84 is rotated and the second character filter 85b is interposed on the optical axis and retreated from the optical axis. The second character filter 85b has the same character as the second character filter 16b in FIG. 1. Because the filter 16b is interposed on the optical axis, the illuminating light from the light source lamp 1 can be reduced.

Further, a plate-like member 87 is fixed on the flange part 12 of the rotary filter 4. In the plate-like member 87, a first character filter 85a is provided and has the same character as the first character filter 16a in FIG. 1. In case the rotary filter 4 moves to the side of the switch 15a, color transmitting filters 5R, 5G and 5B and the first character filter 85a are interposed on the optical axis.

In the embodiment formed as mentioned above, in case the scopes 31A and 31C are connected, the rotary moving control apparatus 17 rotates the rotary solenoid 86 so as to make the character filter 85b retreat from the optical axis. Also, the rotary filter 4 is moved by controlling the motor 11, and the color transmitting filters 5R, 5G and 5B, and the character filter 85a are interposed on the optical axis. Therefore, the white light from the light source lamp 1 is the illuminating light from which infrared rays are removed and then, the illuminating light becomes suitable for the solid state imaging device 46 which is sequentially operated.

On the other hand, in case the scopes 31B, 31D and 31E are connected to the control apparatus 42, the rotary moving control apparatus 17 rotates the rotary solenoid 86 and interposes the character filter 85b on the optical axis. Also, the rotary moving control apparatus 17 controls the motor 11 so as to make the rotary filter 4 retreat from the optical axis. By this operation, the white light from the light source lamp 1 is reduced by the second character filter 85b and fed into the condenser lens 2 so that the incident end surface of the light guide 21 is prevented from burning.

FIGS. 13 to 16 show the third embodiment of the present invention.

Figure 13:
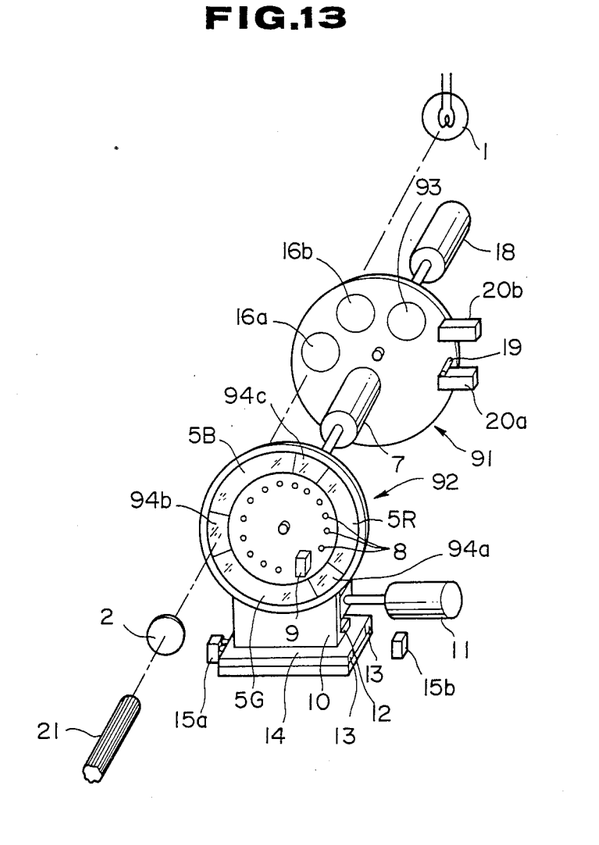

This embodiment is applied to the endoscope for measuring the distribution of the degree of saturation with oxygen of hemoglobin and applied to the light source apparatus of the present invention which can provide suitable illuminating light for the ordinary observation mentioned in the first and the second embodiments.

Between the light guide 21 and the light source lamp 1 of this embodiment, a turret 91 and a rotary filter 92 are provided. In the turret 91, in addition to the first character filter 16a for removing infrared rays mentioned in the first embodiment and the second character filter 16b as a reducing light filter, a band restriction filter 93 is provided in the peripheral direction. This band restriction filter 93 transmits the range of infrared rays more than about 650 nm.

Figure 14:
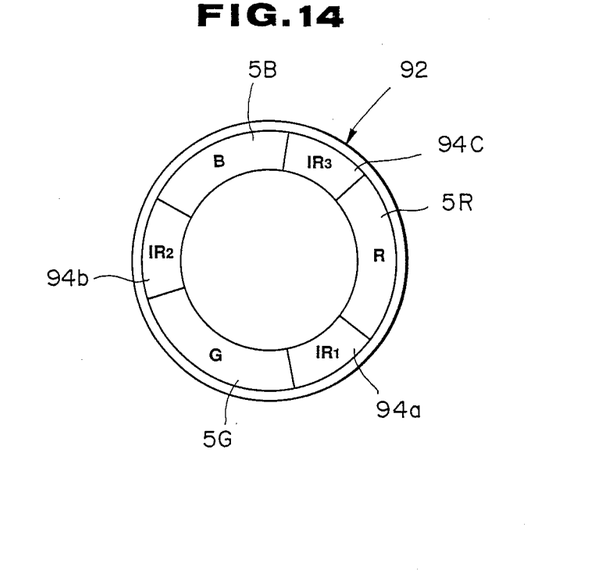
FIG. 14 is an explanatory view showing a rotary filter.
Figure 15:
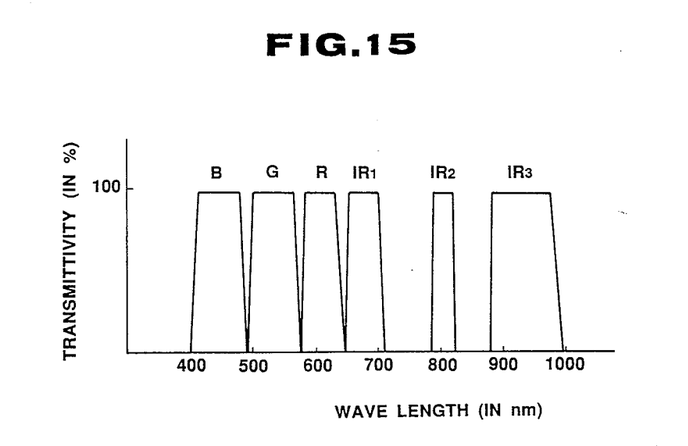
FIG. 15 is an explanatory view showing a transmitting wavelength range of each filter of a rotary filter.

As shown in FIG. 14, in the rotary filter 92 having a discal filter from mentioned above, in addition to the color transmitting filters 5R, 5G and 5B for transmitting the light of each wavelength range of red(R), green(G) and blue(B) for observing in the ordinary visible range mentioned in the first embodiment, in order to convert the changes of the degree of saturation with oxygen of hemoglobin into color pictures, filters 94a, 94b and 94c transmitting the light of specific wavelength ranges $IR_1$, $IR_2$ and $IR_3$ are arranged along the peripheral direction in the order of 5R, 94a, 5G, 94b, 5b and 94c, that is to say, in the order of $R_1$, $IR_1$, G, $IR_2$, B and $IR_3$. Transmitting character of each filter of this rotary filter 92 is shown in FIG. 15.

The other formation is shown as the same as the first embodiment.

The operation of this embodiment formed as mentioned above will be explained in the following.

The operation for observing the picture in an ordinary visible range is the same as the description of the first embodiment.

In case the picture showing the change of the degree of saturation with oxygen of hemoglobin is observed, the band restriction filter 93 is inserted in the optical path of illuminating light. The light of the infrared rays range which has passed through this band restriction filter 93 is color separated in each wavelength range of $IR_1$, $IR_2$ and $IR_3$ by time series and enters the light guide 21. Sections between the filters 5R, 5G and 5B of R, G and B, respectively, become shading periods.

Figure 16:
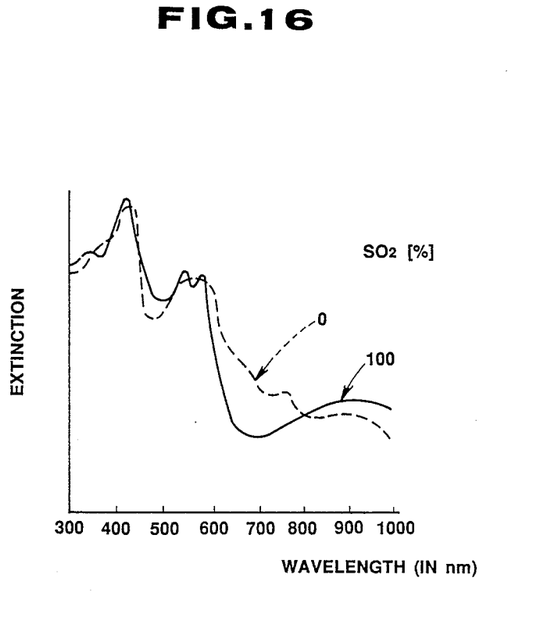
FIG. 16 is an explanatory view showing a scattering reflection spectrum of blood based on the difference of degree of saturation with oxygen of hemoglobin.

The reflected light from an observation part which is illuminated in time series by the light from $IR_1$, $IR_2$ and $IR_3$, is made to be an optical image by the objective 45, and photoelectrically converted by the solid state imaging device 46 as illuminated by the light of R, G and B. The output signal of the solid state imaging device 46 passes through the preamplifier 50 and the switching switches 52, and enters into the frame sequential type processing circuit 56. In the frame sequential type processing circuit 56, the signal passes through the sample holding circuit 61, the γ correcting circuit 62, the A/D conversion circuit 63 and the multiplexer 64, and then a picture of $IR_1$ is written in the R frame memory 65R and a picture of $IR_2$ is written in the G frame memory 65G and a picture of $IR_3$ is written in the B frame memory 65B, respectively. A video signal read from each memory 65R, 65G and 65B is made to convert to an analog signal in the D/A conversion circuits 66, 67 and 68, and a video signal of each wavelength range of $IR_1$, $IR_2$ and $IR_3$ is output from each D/A conversion circuit 66, 67 and 68. Here, as shown in FIG. 16, for example, the scattering reflection (absorption) spectrum of blood having the degree of saturation with oxygen of hemoglobin of "0" and "100" (the ratio of hemoglobin oxide to the whole quantity of hemoglobin: $so_2$) changes with different wavelengths. In this embodiment, the wavelength range of $IR_1$ of filter 94a is in the range of 600 to 700 nm in which an absorbance changes on a large scale with the different degrees of saturation with oxygen, the narrow band of $IR_2$ of filter 94b is in the wavelength centering around 805 nm in which there is almost no variation of absorbance, and the wavelength range of $IR_3$ of filter 94c is in the range of about 900 to 100 nm in which the changing rate of absorbance is relatively small as compared with $IR_1$ but the difference of absorbance caused by the change of the degree of saturation with oxygen can be detected, are artificially colored, respectively. Then, the video signal from respective D/A conversion circuits 66, 67 and 68 mentioned above is processed as an artificial color-difference signal in the matrix circuit 76 of the output circuit 69 and becomes an NTSC video signal in the NTSC encoder 78 through the switching switches 77 so that the difference of the degree of saturation with oxygen of tissue is artificially colored and displayed in the monitor 43.

According to this embodiment, suitable illuminating light can be provided for the scope having the frame sequential type imaging device for ordinary observation, the scope having the synchronous type imaging device for ordinary observation, the fiberscope in which it is possible to observe with the naked eye and the scope having the frame sequential type imaging device measuring the distribution of the degree of saturation with oxygen of hemoglobin.

As above mentioned, according to the present invention, since a plurality of fibers are selectively interposed on the optical axis based on the type of scope to be used and suitable illuminating light for each scope can be provided, a burnout of the light guide can be prevented and there is an effect that the color reproducibility of the picture obtained by these scopes can be improved.

What is claimed is:

1. An endoscope light source apparatus to which a fiberscope or an electronic endoscope can be connected comprising:
   a light source emanating illuminating light;
   an illuminating light emanating end for feeding a connected scope with said illuminating light output from said light source;
   a rotary filter means removably provided on an optical axis connecting said light source and said illuminating light emanating end, having a rotary filter sequentially transmitting light of a specific wavelength of the illuminating light from said light source in case said rotary filter means is inserted on the optical axis; and
   a character changing means having a plurality of character filters and changing a character of the illuminating light from said light source by selectively interposing said character filters on said optical axis corresponding to the connected scope.

2. An endoscope light source apparatus of claim 1, further comprising a rotary moving control means controlling a rotation and transfer of said rotary filter means and controlling interposition of said character filter of said character changing means on the optical axis.

3. An endoscope light source apparatus of claim 2, further comprising a specific wavelength detecting means for detecting a specific wavelength transmitted in said rotary filter means and a character detecting means for detecting a character changed by said character changing means; and said specific wavelength detecting means and said character detecting means output a detecting result to said rotary moving control means.

4. An endoscope light source apparatus of claim 3, further comprising a discriminating means detecting a type of the connected scope, and said discriminating means outputs a discriminated result to said rotary moving control means.

5. An endoscope light source apparatus of claim 1, 2, 3 or 4, wherein the rotary filter means comprises:
   said rotary filter;
   a rotary driving means for rotating said rotary filter; and
   a moving means for removably moving said rotary filter on said optical axis.

6. An endoscope light source apparatus of claim 5, wherein three primary colors filters, located in a discal filter frame, transmit three primary colors of light for obtaining a color picture and are provided in a peripheral direction.

7. An endoscope light source apparatus of claim 5, wherein said rotary filter comprises in a peripheral direction;
   three primary color filters transmitting three primary colors of light for obtaining a color picture, said three primary color filters located in a discal filter frame;
   a first filter transmitting a wavelength band in which an absorbance of hemoglobin changes with different degrees of saturation with oxygen; and
   a second filter transmitting a wavelength band in which the absorbance of hemoglobin does not change with different degrees of saturation with oxygen.

8. An endoscope light source apparatus of claim 1, 2, 3 or 4, wherein the character changing means is formed of a character changing filter means changing a character of illuminating light and a driving means driving said character changing filter means.

9. An endoscope light source apparatus of claim 8, wherein said character changing filter means is provided with an infrared ray removing filter removing a wavelength range of infrared rays from said illuminating light and a reducing light filter reducing a quantity of said illuminating light, said infrared ray removing filter and said reducing light filter provided in a discal filter frame in a peripheral direction.

10. An endoscope light source apparatus of claim 9, wherein said character changing filter means, further comprising a band restriction filter in the peripheral direction removing a wavelength range of visible rays and transmitting a wavelength range of infrared rays.

11. An endoscope light source apparatus of claim 8, wherein said character changing filter means comprises:
   an arm;
   a light reducing filter for reducing a quantity of illuminating light provided in one end of the arm; and
   an infrared ray removing filter interposed on the optical axis with said rotary filter means removing a wavelength range of infrared rays from the illuminating light.

12. An endoscope light source apparatus of claim 11, wherein a rocking motor as said driving means is provided in another end of the arm.

* * * * *